(12) United States Patent
Klauber et al.

(10) Patent No.: US 9,957,212 B2
(45) Date of Patent: May 1, 2018

(54) PROCESS FOR PRODUCING 2,5-DIHALOPHENOLETHERS

(71) Applicant: BASF SE, Ludwigshafen (DE)

(72) Inventors: Eric George Klauber, Bad Duerkheim (DE); Michael Rack, Eppelheim (DE); Thomas Zierke, Boehl-Iggelheim (DE); Nicole Holub, Mannheim (DE); Gerald Schmelebeck, Buna, TX (US); Junmin Ji, Beaumont, TX (US); David Cortes, Quincy, IL (US)

(73) Assignee: BASF SE, Ludwigshafen (DE)

(*) Notice: Subject to any disclaimer, the term of this patent is extended or adjusted under 35 U.S.C. 154(b) by 67 days.

(21) Appl. No.: 15/119,654

(22) PCT Filed: Feb. 19, 2015

(86) PCT No.: PCT/EP2015/053453
§ 371 (c)(1),
(2) Date: Aug. 17, 2016

(87) PCT Pub. No.: WO2015/124651
PCT Pub. Date: Aug. 27, 2015

(65) Prior Publication Data
US 2017/0008824 A1 Jan. 12, 2017

Related U.S. Application Data

(60) Provisional application No. 61/942,656, filed on Feb. 21, 2014.

(30) Foreign Application Priority Data

Apr. 2, 2014 (EP) ..................... 14163258

(51) Int. Cl.
C07C 37/02 (2006.01)
C07C 41/16 (2006.01)
C07C 37/62 (2006.01)
C07C 51/16 (2006.01)
C07C 51/285 (2006.01)

(52) U.S. Cl.
CPC .............. *C07C 41/16* (2013.01); *C07C 37/02* (2013.01); *C07C 37/62* (2013.01); *C07C 51/16* (2013.01); *C07C 51/285* (2013.01)

(58) Field of Classification Search
None
See application file for complete search history.

(56) References Cited

U.S. PATENT DOCUMENTS 4,232,172 A 11/1980 Becher et al.

FOREIGN PATENT DOCUMENTS

WO WO-2001/83417 11/2001

OTHER PUBLICATIONS

Cresp et al., "Synthesis of Piloquinone, a Metabolite of *Streptomyces pilosus* Ettlinger," Journal of the Chemical Society, 1974, pp. 2435-2447.
Schmitz et al., "Ortho-Specific Bromination of Phenols," Journal für praktische Chemie, 1985, vol. 327, No. 6, pp. 998-1006.
European Search Report dated Sep. 11, 2014 for European Application No. 14163258.8.
International Search Report dated Apr. 23, 2015 for International Application No. PCT/EP2015/053453.
International Preliminary Report on Patentability dated Aug. 23, 2016 for International Application No. PCT/EP2015/053453.

*Primary Examiner* — Sudhakar Katakam
*Assistant Examiner* — Jennifer C Sawyer
(74) *Attorney, Agent, or Firm* — Brinks Gilson & Lione

(57) ABSTRACT

The present invention relates to a process for providing a compound of formula (IV):

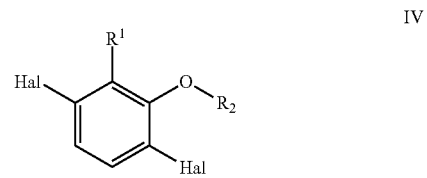

IV wherein $R^1$ and $R^2$ are each independently $C_1$-$C_4$ alkyl, and Hal is independently Cl or Br, the process comprising the steps of: (i) reacting a compound of formula (II)

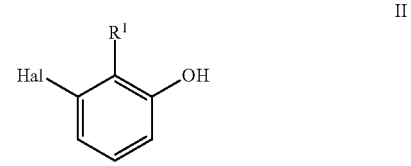

II wherein $R^1$ and Hal is defined as above, to obtain a compound of formula (III)

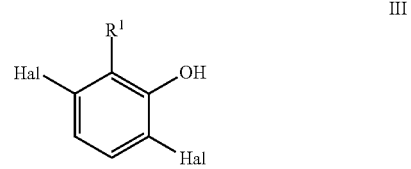

III wherein $R^1$ and Hal is defined as above, and (ii) reacting the compound of formula (III) to obtain the compound of formula (IV).

7 Claims, No Drawings

PROCESS FOR PRODUCING 2,5-DIHALOPHENOLETHERS

The present invention relates to a process for producing 2,5-dihalophenolethers. In particular, the present invention relates to a reaction sequence for obtaining 2,5-dihalophenolethers starting from readily available starting materials. The products obtained according to the invention can in preferred embodiments be used for providing 2-5-dihalo substituted salicylic acid derivatives such as the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid. The estimated global demand for dicamba in 2012 was about 12.000 metric tons per year. However, it is expected that the global demand for dicamba will increase significantly.

Dicamba is typically produced on an industrial scale via 2,5-dichlorophenol and using carboxylation under Kolbe-Schmitt conditions, methylation and subsequently saponification/acidification. 2,5-Dichlorophenol in turn can be obtained from 1,4-dichlorobenzene or 1,2,4-trichlorobenzene. A synthetic route via 1,4-dichlorobenzene involving nitration and subsequent diazotation may, however, be undesired for use on an industrial scale. A synthetic route via 1,2,4-trichlorobenzene may suffer from limited availability of this starting material and from the formation of several byproducts which are formed in the synthesis of 2,5-dichlorophenol.

In order to meet the increasing market demand for compounds such as dicamba, there is a need in the art for alternative processes providing acceptable yield and/or relying on alternative and readily available starting materials.

SUMMARY OF THE INVENTION

In view of the above, it is the object of the present invention to provide a process suitable for providing 2,5-dihalo substituted phenolether derivatives in alternative reaction sequences. It is a further object of the invention to provide a process for obtaining 2,5-dihalo substituted phenolether derivatives with acceptable yield. According to a further object of the present invention, alternative reaction sequences for obtaining 2,5-dihalophenolether derivatives are provided starting from alternative starting materials that are readily available. It is a further object of the present invention to implement the processes for the synthesis of 2,5-dihalophenolether derivatives, especially 3,6-dihalo salicylic acid derivatives such as dicamba, on an industrial scale.

The present invention is directed to a reaction sequence for obtaining 2-5-dihalophenolether derivatives. In particular, the present invention relates to a process for providing a compound of formula (IV):

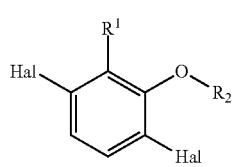

wherein $R^1$ and $R^2$ are each independently $C_1$-$C_4$ alkyl, and Hal is independently Cl or Br.

The process comprises the steps of:
(i) reacting a compound of formula (II)

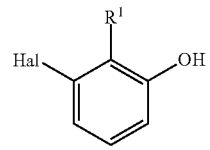

wherein $R^1$ and Hal is defined as above, in the presence of a chlorination or bromination agent to obtain a compound of formula (III)

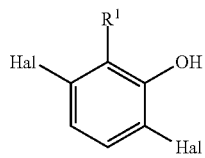

wherein $R^1$ and Hal is defined as above, and
(ii) reacting the compound of formula (III) to obtain the compound of formula (IV).

Step (i) is carried out in the presence of a chlorinating agent or bromination agent. The chlorination agent may be selected from sulfurylchloride, N-chlorosuccinimide (NCS), N-chloroalkylamine, N-chlorodialkylamine, and N-dichloroalkylamine. The bromination agent may be selected from sulfurylbromide, N-bromosuccinimide (NBS), N-bromoalkylamine, N-bromodialkylamine, and N-dibromoalkylamine.

In some embodiments, step (i) is optionally carried out in the further presence of a secondary amine.

Furthermore, step (ii) is carried out in the presence of a base and an alkylating agent. The as defined above.

In some embodiments, the above compound of formula (II) may be obtained by reacting a compound of formula (I)

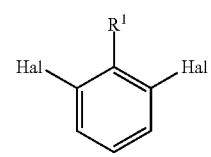

wherein $R^1$ and Hal is as defined above, in the presence of an alkali metal hydroxide or alkali metal alkoxide.

In some embodiments, the 2,5-dihalophenolether derivatives obtainable in accordance with the invention may be reacted further to provide 2,5-dihalo salicylic acid derivatives. In particular, the present invention also relates to processes as defined above, further comprising the step of:
(iii) reacting a compound of formula (IV) as defined above in the presence of an oxidation agent to obtain a compound of formula (V):

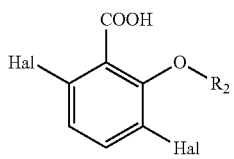

wherein $R^2$ and Hal is as defined above.

The present invention also relates to a process comprising the steps:

(i) reacting a compound of formula (I)

I

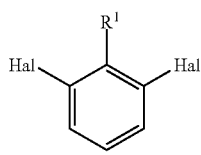

in the presence of an alkali metal hydroxide or alkali metal alkoxide to obtain a compound of formula (II)

II

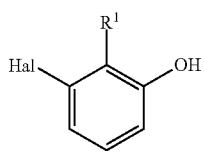

(ii) reacting the compound of formula (II) to obtain a compound of formula (III)

III

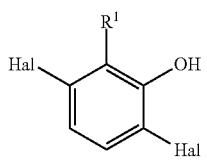

(iii) reacting the compound of formula (III) to obtain a compound of formula (IV)

IV

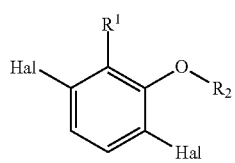

and (iv) reacting the compound of formula (IV) to obtain a compound of formula (V)

V

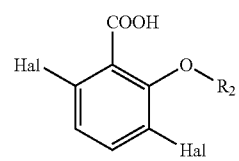

wherein $R^1$ and $R^2$ are each independently $C_1$-$C_4$ alkyl, such as methyl, and Hal is independently Cl or Br, such as Cl.

In some embodiments of the present invention, $R^1$ is methyl. In further embodiments of the present invention, $R^2$ is methyl. In other embodiments of the present invention, $R^1$ is methyl and $R^2$ is methyl.

In some embodiments of the present invention Hal is Cl.

In some embodiments, of the present invention, $R^1$ is methyl, $R^2$ is methyl, and Hal is Cl.

In certain embodiments of the present invention, the above process is employed for the synthesis of dicamba. In these embodiments, the compound of formula (V) is

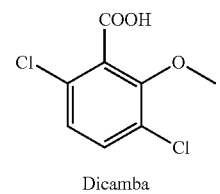

Dicamba

Further embodiments of the present invention are apparent from the following detailed description and the attached claim set.

DETAILED DESCRIPTION OF THE INVENTION

In the following, illustrative embodiments of the present invention are described in more detail.

In the context of the present invention, the term "equivalent" refers to molar equivalents.

The term "halo" refers in the context of the present invention to a halogen atom selected from Cl and Br.

As noted above, the present invention relates to a process for providing a compound of formula (IV):

IV

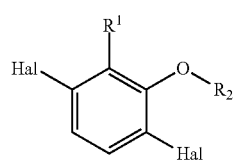

wherein $R^1$ and $R^2$ are each independently $C_1$-$C_4$ alkyl, and Hal is independently Cl or Br, comprising the step of:

(i) reacting a compound of formula (II) to obtain a compound of formula (III), wherein $R^1$ is respectively $C_1$ to $C_4$ alkyl, such as methyl, and Hal is Cl or Br, such as Cl.

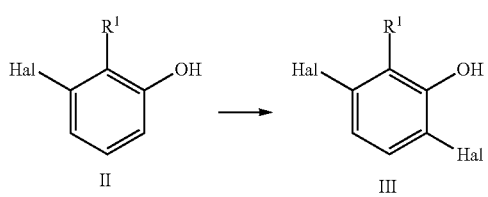

II → III

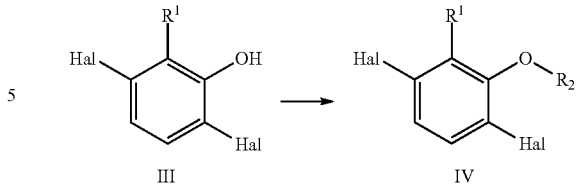

III → IV

Step (i) relates to ortho-chlorination or ortho-bromination of phenol derivatives of formula (II). Illustrative reaction conditions can be found e.g. in E. Schmitz et al., Journal f. prakt. Chemie, 327(6), 1985, 998-1006. The reaction is carried out in the presence of a chlorination agent or bromination agent. The chlorination agent may be selected from sulfurylchloride, N-chlorosuccinimide (NCS), N-chloroalkylamine, N-chlorodialkylamine, and N-dichloroalkylamine, wherein the alkyl in the alkylamine groups or dialkylamine groups may be independently e.g. a $C_1$ to $C_4$ alkyl group. Illustrative chlorination agents in addition to sulfurylchloride and NCS include but are not limited to tert-butyl-NHCl, $Me_2NCl$, or MeNHCl. The bromination agent may be selected from sulfurylbromide, N-bromosuccinimide (NBS), N-bromoalkylamine, N-bromodialkylamine, and N-dibromoalkylamine, wherein the alkyl in the alkylamine groups or dialkylamine groups may be independently e.g. a $C_1$ to $C_4$ alkyl group. Illustrative bromination agents in addition to sulfurylbromide and NBS include but are not limited to tert-butyl-NHBr, $Me_2NBr$, or MeNHBr.

The chlorinating agent or bromination agent is typically employed in about stoichiometric amounts. Thus, about 1.0 to about 1.2, optionally about 1.0 to 1.1, such as about 1.0 equivalents of chlorination agent is employed per one equivalent of the compound of formula (II).

The above reaction is typically carried out at neutral pH. In some embodiments, minor amounts of a base may be present. The base is typically a secondary amine such as but not limited to di(iso-butyl)amine. Suitable amounts include about 0.002 to about 0.02 equivalents, optionally about 0.005 to about 0.01 equivalents of secondary amine per one equivalent of the compound of formula (II).

Step (i) is typically carried out in the presence of an organic solvent. Illustrative solvents include but are not limited to optionally halogenated aliphatic or aromatic solvents, such as toluene, heptane or chlorobenzene.

Step (i) is typically carried out at elevated temperature. Thus, in one embodiment, the reaction is carried out at about 50° C. to about 90° C., optionally at about 60° C. to about 80° C.

Depending on the chlorination agent or bromination agent, the reaction may afford the compound of formula (III) in deprotonated form, especially when an amine is used as the chlorination agent or bromination agent. In these cases, the compound of formula (III) is finally obtained by acidification using a suitable acid, such as HCl or $H_2SO_4$.

In a second reaction step according to the invention, the compound of formula (III) obtained above is alkylated. Thus, the process of the invention further comprises the step of:

(ii) reacting the compound of formula (III) to obtain the compound of formula (IV).

Step (ii) is carried out in the presence of an alkylating agent. The alkylating agent is typically selected from $(R^2)_2SO_4$, $(R^2O)_2CO$, $R^2I$, $R^2Br$, and $R^2Cl$, wherein $R^2$ is as defined above. For example, $R^2$ may be methyl.

The alkylating agent is employed in at least stoichiometric amounts. Thus, about 1.0 to about 1.6 equivalents of alkylating agent, optionally about 1.2 to about 1.4 equivalent of alkylating agent are typically employed per one equivalent of the compound of formula (III).

Furthermore, step (ii) is carried out in the presence of a base. Suitable bases include inorganic and organic bases. Illustrative inorganic bases include but are not limited to carbonates, such as sodium carbonate or potassium carbonate, hydroxides, such as sodium or potassium hydroxide (aqueous), hydrides, such as sodium hydride or potassium hydride, or alcoholates, such as potassium tert-butanolate. Illustrative organic bases include but are not limited to amines, such as tertiary amines, e.g. triethylamine, N,N-diisopropylethylamine or 1,8-diazabicycloundec-7-ene (DBU). An excess of base is typically employed. Thus, step (ii) may be carried out in the presence of about 2.0 to about 3.0, optionally about 2.1 to about 2.5 equivalents of base per one equivalent of the compound of formula (III).

The reaction according to step (ii) is typically carried out in an organic solvent. Suitable solvents include aprotic solvents, including but not limited to acetone, dichloroethane, dichloromethane, dimethylformamide (DMF), tetrahydrofuran (THF), and dimethyl sulfoxide (DMSO).

Step (ii) may be carried out at elevated temperature. For example, the reaction may be carried out at about 40° C. to the reflux temperature of the solvent used. In some embodiments, the reaction is carried out at about 40° C. to about 80° C., such as about 50° C. to about 70° C.

As outline above, a compound of formula (II) is employed as a starting material for the reaction sequence according to the invention. The present invention is not specifically limited as regards how the compound of formula (II) is obtained. In some embodiments, the above compound of formula (II) may be obtained by reacting a compound of formula (I), wherein $R^1$ and Hal is as defined above, in the presence of an alkali metal hydroxide or alkali metal alkoxide.

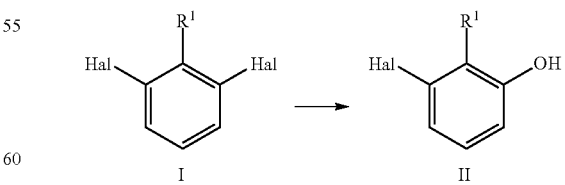

I → II

Suitable alkali metal hydroxides include e.g. sodium hydroxide or potassium hydroxide. Suitable alkali metal alkoxides include e.g. sodium or potassium methoxide or ethoxide. The hydroxides or alkoxides are provided in aqueous form e.g. in the form of an aqueous solution having a concentration of about 50% to about 85%, such as e.g. a 85% aqueous solution of KOH. An excess of hydroxide or alkoxide is typically used. Thus, the reaction may be carried out in the presence of about 2.0 to about 4.0, optionally about 2.5 to about 3.5 equivalents, such as about 3.0 equivalents of hydroxide or alkoxide per one equivalent of the compound of formula (I).

The reaction is carried out in a solvent e.g. an alcohol such as methanol. Alternative solvents include e.g. DMSO, DMF or diethylene glycol. The reaction is carried out at elevated temperature, such as about 180° C. to about 200° C. Further illustrative reaction conditions are described e.g. in EP 0 831 083, EP 0 941 982, or WO 01/83417.

In some embodiments, the compounds of formula (IV) obtainable in accordance with the invention may be reacted by means of oxidation to provide 2,5-dihalo salicylic acid derivatives, such as 2,5-dichloro salicylic acid derivatives. In particular, the present invention also relates to processes as defined above, further comprising the step of:

(iii) reacting a compound of formula (IV) as defined above in the presence of an oxidation agent to obtain a compound of formula (V), wherein $R^2$ and Hal is as defined above:

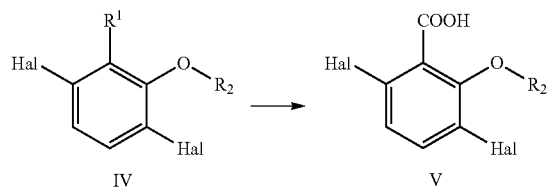

Oxidation agents for oxidizing alkyl side chains of aromats so as to obtain benzoic acids are well known in the art. For example, $KMnO_4$ may be employed for the oxidation reaction. Other suitable oxidation agents include but are not limited to sodium hypochlorite, urea-hydrogen peroxide complex, potassium peroxomonosulfate (Oxone), or oxygen ($O_2$) in combination with suitable catalysts such as Co or Mn based catalysts.

An excess of oxidation agent is typically used. Thus, the oxidation agent may be employed in an amount of about 3.0 to about 5.0 equivalents, optionally about 3.5 to about 4.5 equivalents, such as about 4.0 equivalents per one equivalent of the compound of formula (IV).

The reaction is carried out in an inert solvent such as water or an alcohol water mixture, e.g. a 1:1 mixture of water and tert-butanol. Furthermore, the reaction is typically carried out at elevated temperature, such as about 60° C. to about 100° C., optionally about 75° C. to about 85° C.

In the following, the present invention is illustrated in more detail by means of a working example.

WORKING EXAMPLE

One equivalent of 1,3-dichloro-2-methylbenzene is reacted with 3.0 equivalents of aqueous KOH (85%) in the presence of 10.0 equivalents of methanol. The reaction was carried out at 200° C. After 20 hours 3-chloro-2-methylphenol was obtained with an isolated yield of 86%.

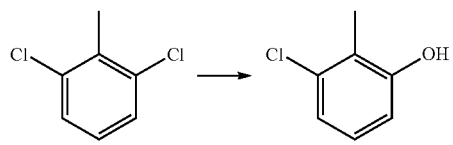

1-3-dichloro-2-methylbenzene is a compound of formula (I) according to the invention in which $R^1$ is methyland Hal is Cl. Furthermore, 3-chloro-2-methylphenol is a compound of formula (II) according to the invention in which $R^1$ is methyl and Hal is Cl.

Subsequently, one equivalent of 3-chloro-2-methylphenol was reacted with 1.0 equivalents of sulfurylchloride in the presence of 0.005 to 0.01 equivalents of di(iso-butyl)amine. The reaction was carried out in toluene at a temperature of 70° C. After 2 hours 3-6-dichloro-2-methylphenol was obtained with an isolated yield of 87%.

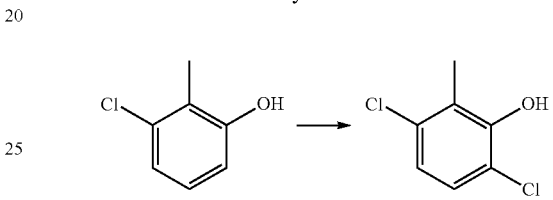

3,6-dichloro-2-methylphenol is a compound of formula (III) according to the invention in which $R^1$ is methyl and Hal is Cl.

Then, one equivalent of 3,6-dichloro-2-methylphenol was reacted with 1.3 equivalents of dimethylsulfate in the presence of 2.3 equivalents of potassium carbonate. The reaction was carried out in acetone at a temperature of 56° C. After 3 hours 1,4-dichloro-2-methoxy-methylbenzene was obtained with an isolated yield of 91%.

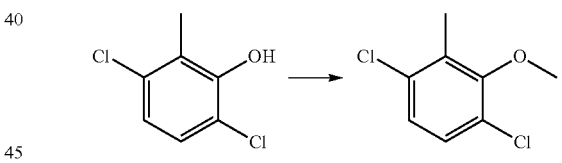

1,4-dichloro-2-methoxy-methylbenzene is a compound of formula (IV) according to the invention in which $R^1$ and $R^2$ are both methyl, and Hal is Cl.

Finally, one equivalent of 1,4-dichloro-2-methoxy-methylbenzene was reacted with 4.0 equivalents of KMnO4 in a 1:1 mixture of tert-butanol at 80° C. After 10 to 12 hours dicamba was obtained with an isolated yield of 83%.

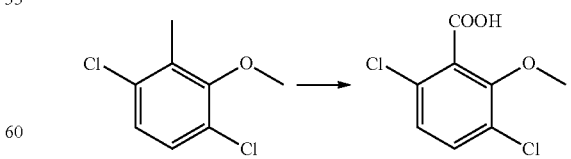

Dicamba is a compound of formula (V) according to the invention in which $R^2$ is methyl, and Hal is Cl.

As can be seen, the reaction sequence described above provides 2,5-dihalophenolether derivatives in high yield starting from simple starting materials. In a preferred embodiment, the present invention provides a synthetic route towards dicamba starting from readily available starting material in excellent yields. The processes according to the invention can be carried out on an industrial scale.

The invention claimed is:

1. A process of making a compound of formula (V)

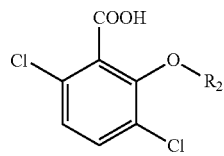

V wherein $R^2$ is $C_1$-$C_4$ alkyl;
comprising the steps of:
(i) reacting a compound of formula (II)

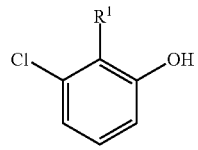

II in the presence of a chlorination agent to obtain a compound of formula (III)

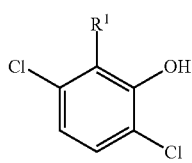

III (ii) reacting the compound of formula (III) to obtain the compound of formula (IV)

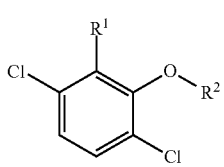

IV and
(iii) reacting the compound of formula (IV), wherein $R^1$ and $R^2$ are each independently $C_1$-$C_4$ alkyl, in the presence of an oxidation agent to obtain the compound of formula (V).

2. The process according to claim 1, wherein step (i) is carried out in the presence of a chlorinating agent selected from sulfurylchloride, N-chlorosuccinimide (NCS), N-chloroalkylamine, N-chlorodialkylamine, and N-dichloroalkylamine, optionally in the further presence of a secondary amine.

3. The process according to claim 1, wherein step (ii) is carried out in the presence of a base and an alkylating agent selected from $(R^2)_2SO_4$, $(R^2O)_2CO$, $R^2I$, $R^2Br$, and $R^2Cl$.

4. The process according to claim 1, wherein the compound of formula (II) is obtained by reacting a compound of formula (I)

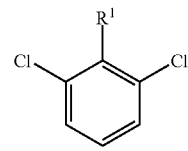

I in the presence of an alkali metal hydroxide or alkali metal alkoxide.

5. The process according to claim 1, wherein
(a) $R^1$ is methyl, and/or
(b) $R^2$ is methyl.

6. The process according to claim 1, wherein the compound of formula (V) is

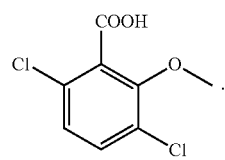

7. The process according to claim 1, comprising the steps:
(i) reacting a compound of formula (I)

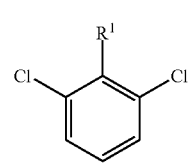

I in the presence of an alkali metal hydroxide or alkali metal alkoxide to obtain a compound of formula (II)

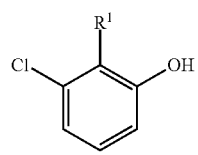

II (ii) reacting the compound of formula (II) to obtain a compound of formula (III)

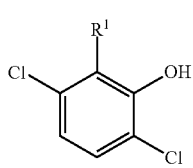

III (iii) reacting the compound of formula (III) to obtain a compound of formula (IV)

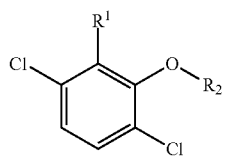
IV
and
(iv) reacting the compound of formula (IV) to obtain a compound of formula (V)
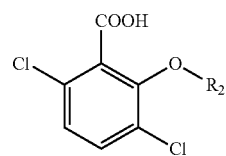
V
wherein $R^1$ and $R^2$ are each independently $C_1$-$C_4$ alkyl.
* * * * *